(12) United States Patent
Tsuboyama et al.

(10) Patent No.: US 11,686,698 B2
(45) Date of Patent: Jun. 27, 2023

(54) REDUCING GAS DETECTION MATERIAL AND REDUCING GAS DETECTION SENSOR

(71) Applicant: CANON KABUSHIKI KAISHA, Tokyo (JP)

(72) Inventors: Akira Tsuboyama, Machida (JP); Koji Yano, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 1047 days.

(21) Appl. No.: 16/395,647

(22) Filed: Apr. 26, 2019

(65) Prior Publication Data

US 2019/0346392 A1    Nov. 14, 2019

(30) Foreign Application Priority Data

May 14, 2018 (JP) .................. 2018-093370
May 14, 2018 (JP) .................. 2018-093371

(51) Int. Cl.
  *G01N 27/18* (2006.01)
  *G01N 21/78* (2006.01)
  *G01N 33/00* (2006.01)
  *H01M 8/04007* (2016.01)
  *H01M 8/22* (2006.01)

(52) U.S. Cl.
  CPC ............ *G01N 27/18* (2013.01); *G01N 21/783* (2013.01); *G01N 33/005* (2013.01); *G01N 33/0014* (2013.01); *H01M 8/04074* (2013.01); *H01M 8/22* (2013.01)

(58) Field of Classification Search
  CPC .. G01N 27/18; G01N 21/783; G01N 33/0014; G01N 33/005; G01N 27/125; G01N 21/78; H01M 8/04074; H01M 8/22; H01M 2250/20; H01M 8/04313; H01M 8/04686; Y02E 60/50; Y02T 90/40
  USPC ........................................... 73/25.03
  See application file for complete search history.

(56) References Cited

U.S. PATENT DOCUMENTS

| 4,351,182 | A | 9/1982 | Schmidberger |
| 5,980,833 | A | 11/1999 | Higaki et al. |
| 10,156,536 | B2 | 12/2018 | Fujii et al. |
| 10,281,420 | B2 | 5/2019 | Muraoka et al. |

(Continued)

FOREIGN PATENT DOCUMENTS

| CA | 2666370 A1 * | 4/2008 | ............ G01N 27/04 |
| CN | 1174992 | 3/1998 | |

(Continued)

OTHER PUBLICATIONS

Jun Seop Lee et al., Porous palladium coated conducting polymer nanoparticles for ultrasensitive hydrogen sensors, Nanoscale, 205, 7, (20665-20673) (Year: 2015).*

(Continued)

*Primary Examiner* — Marrit Eyassu
(74) *Attorney, Agent, or Firm* — Venable LLP

(57) ABSTRACT

Provided is a reducing gas detection sensor which has sensitivity improved as compared to that of the related art, and in which power consumption is decreased. The reducing gas detection sensor includes: a reducing gas detection material including a palladium compound and a carbon compound, and having reactivity with a reducing gas; and a unit configured to measure a conductivity of the reducing gas detection material.

19 Claims, 6 Drawing Sheets

(56) References Cited

U.S. PATENT DOCUMENTS

| | | | |
|---|---|---|---|
| 10,309,916 | B2 | 6/2019 | Muraoka et al. |
| 10,466,218 | B2 | 11/2019 | Swager et al. |
| 2007/0181426 | A1 | 8/2007 | Fleischer et al. |
| 2009/0127100 | A1 | 5/2009 | Fleischer et al. |
| 2016/0377569 | A1 | 12/2016 | Rajaraman et al. |
| 2020/0225201 | A1 | 7/2020 | Swager et al. |

FOREIGN PATENT DOCUMENTS

| | | | | |
|---|---|---|---|---|
| CN | 1174992 | A | | 3/1998 |
| CN | 1997889 | | | 7/2007 |
| CN | 1997889 | A | | 7/2007 |
| CN | 107315033 | | | 11/2007 |
| CN | 105510400 | A | * 4/2016 | ............. G01N 27/12 |
| CN | 107102032 | | | 8/2017 |
| CN | 107102032 | A | | 8/2017 |
| CN | 107315033 | A | | 11/2017 |
| CN | 107315034 | | | 11/2017 |
| CN | 107315034 | A | | 11/2017 |
| JP | 55-147344 | A | | 11/1980 |
| JP | 57-044846 | A | | 3/1982 |
| JP | 60-21147 | A | | 2/1985 |
| JP | 6-172778 | A | | 7/1993 |
| JP | 8-510548 | | | 11/1996 |
| JP | 8-510548 | A | | 11/1996 |
| JP | 9-269306 | A | | 10/1997 |
| JP | 2005-091253 | A | | 4/2005 |
| JP | 2007-225299 | A | | 9/2007 |
| JP | 2009-008476 | A | | 1/2009 |
| JP | 2009-229369 | A | | 10/2009 |
| JP | 2015-194407 | A | | 11/2015 |
| JP | 2016-045036 | A | | 4/2016 |
| JP | 2017-508965 | A | | 3/2017 |
| KR | 20170114985 | A | * 10/2017 | |
| WO | 94/17390 | A1 | | 8/1994 |
| WO | 2004/046705 | A1 | | 6/2004 |
| WO | WO-2004046705 | A1 | * 6/2004 | ........... G01N 27/125 |
| WO | 2015/178994 | A2 | | 11/2015 |

OTHER PUBLICATIONS

Aniruddh B. Yadav et al., Particle size effects on the hydrogen sensing properties of Pd/ZnO Schottky contacts fabricated by sol-gel method, Jul. 8, 206, ScienceDirect, International Journal of Hydrogen Energy 42(207)786-794 (Year: 2016).*

First Office Action in Chinese Application No. 201910395676.8 (dated Feb. 2022).

Notice of Reasons for Refusal in Japanese Application No. 2018-093371 (dated Jun. 2022).

Extended European Search Report in European Application No. 19173502.6 (dated Sep. 2020).

Hideo Okamoto et al., "Formation of Thin Film of PdO and Their Electric Properties," 6 Japan. J. Appl. Phys. 779 (1967).

Notice of Reasons for Refusal in Japanese Application No. 2018-093371 (dated Jan. 2022).

Notice of Reasons for Refusal in Japanese Application No. 2018-093370 (dated Feb. 2022).

Young Tack Lee et al., "Hydrogen Gas Sensing Properties of PdO Thin Films with Nano-Sized Cracks," 21 Nanotech. 165503 (5pp) (2010).

Nataliya S. Nikolaeva et al., "Bilayer Structures Based on Metal Phthalocyanine and Palladium Layers for Selective Hydrogen Detection," 42(47) Int. J. Hydrog. Energy 28640-28646 (Oct. 2017) (XP085277787).

Jun Seop Lee et al., "Porous Palladium Coated Conducting Polymer Nanoparticles for Ultrasensitive Hydrogen Sensors," 7(48) Nanoscale 20665-20673 (2015) (XP055606566).

Y.M. Sabri et al., "QCM Based Mercury Vapor Sensor Modified with Polypyrrole Supported Palladium," 160 Sensors and Actuators B 616-622 (Aug. 2011) (XP028110946).

Partial European Search Report in European Application No. 19173502.6 (dated May 2020).

Third Office Action in Chinese Application No. 201910395676.8 (dated Mar. 2023).

* cited by examiner

REDUCING GAS DETECTION MATERIAL AND REDUCING GAS DETECTION SENSOR

BACKGROUND OF THE INVENTION

Field of the Invention

The present invention relates to a reducing gas detection material and a reducing gas detection sensor using the reducing gas detection material.

Description of the Related Art

A reducing gas is a compound serving as a gas at normal temperature, which has a strong reducing action and has a property of reducing a compound that is easily reduced when being brought into contact therewith. Specific examples of the reducing gas include hydrogen, formaldehyde, carbon monoxide, and ethylene. In particular, hydrogen has started to be utilized as a fuel for fuel-cell vehicles and household fuel cells and is expected as an energy source. Those reducing gases have been widely used for industrial purposes, but have inflammability and explodability, and some of the gases have an effect on human bodies. Therefore, from the viewpoint of safety management, it is required that the leakage of those reducing gases outside a tank, a cylinder, a pipe, applied equipment, and the like, in which the reducing gases are stored, be detected.

In Japanese Patent Application Laid-Open No. 2007-225299, as a sensor configured to detect a hydrogen gas having a reducing property, there is described an optical sensor that is changed in color through a reaction with a hydrogen gas. Specifically, there is disclosed a sensor in which palladium oxide is used for a reactive layer that reacts with hydrogen, and for example, palladium, platinum, or gold is deposited as a catalyst metal layer on the reactive layer.

In Nanotechnology, 21, 165503 (5 pp), 2010, there is described a hydrogen gas detection sensor using a palladium oxide thin film in a reaction site. In Nanotechnology, 21, 165503 (5 pp), 2010, the hydrogen gas detection sensor is used as a reducing gas detection sensor configured to detect a change in resistance (electrical conductivity) caused by a change in resistance (electrical conductivity) of the palladium oxide film through an irreversible reduction reaction between palladium oxide and a hydrogen gas.

In order to detect a reducing gas in the atmosphere, a sensor configured to detect the reducing gas with high sensitivity and accuracy is required.

However, in the sensor disclosed in Japanese Patent Application Laid-Open No. 2007-225299, a user visually determines a degree of change in color of a coloring material, and hence uncertainty is involved. There is also known a method involving optically detecting a change in color. However, in this case, there is a risk in that the sensor may be enlarged. In addition, due to the use of a change in color, there is a problem in that the sensor needs to be arranged at a place in which the user can visually recognize the change in color.

In addition, in the reducing gas detection sensor that utilizes a change in electrical characteristics of a reactive layer as described in Nanotechnology, 21, 165503 (5 pp), 2010, sensitivity is one of important parameters for determining power consumption of the sensor. In general, when the sensitivity of the sensor is high, a change in electrical conductivity caused by contact of the reaction site with the reducing gas is increased. Therefore, the electrical conductivity of the reaction site before reacting with the reducing gas can be designed to be small. With such design, the power consumption of the sensor in a normal state in which the reducing gas is not detected can be decreased.

In Nanotechnology, 21, 165503 (5 pp), 2010, there is described that the sensitivity S of the hydrogen gas detection sensor determined by the following expression (I) is about 45, and hence the sensitivity of the sensor described in Nanotechnology, 21, 165503 (5 pp), 2010 cannot be said to be sufficient:

$$S=(G_H-G_N)/G_N \quad (I)$$

where $G_H$ represents an electrical conductivity in the presence of hydrogen, and $G_N$ represents an electrical conductivity in the absence of hydrogen.

SUMMARY OF THE INVENTION

In view of the above-mentioned problems, an object of the present invention is to provide a reducing gas detection material having reactivity with a reducing gas, a method of detecting a reducing gas through use of the reducing gas detection material, and a reducing gas detection sensor which has sensitivity improved as compared to that of the related art, and in which power consumption is decreased.

The above-mentioned object can be achieved by the present invention. That is, according to one aspect of the present invention, there is provided a reducing gas detection material including a palladium compound and a carbon compound, and having reactivity with a reducing gas.

According to another aspect of the present invention, there is provided a reducing gas detection sensor including: the reducing gas detection material according to the above-mentioned aspect of the present invention; and a unit configured to measure a conductivity of the reducing gas detection material.

According to still another aspect of the present invention, there is provided a moving body including the reducing gas detection sensor according to the above-mentioned aspect of the present invention mounted thereon.

According to yet still another aspect of the present invention, there is provided a method of producing a reducing gas detection material, the method including subjecting a mixture of a palladium compound and a carbon compound to heat treatment.

According to yet still another aspect of the present invention, there is provided a method of detecting a reducing gas, the method including detecting a change in electrical conductivity of the reducing gas detection material according to the above-mentioned aspect of the present invention caused by a reaction with a reducing gas.

As described above, according to the present invention, the reducing gas detection material which can improve sensitivity as compared to that of the related art and can decrease power consumption, and further exhibits a short response time, when being used in a sensor configured to detect a reducing gas, can be provided.

Further features of the present invention will become apparent from the following description of exemplary embodiments with reference to the attached drawings.

DESCRIPTION OF THE EMBODIMENTS

Figure 1:
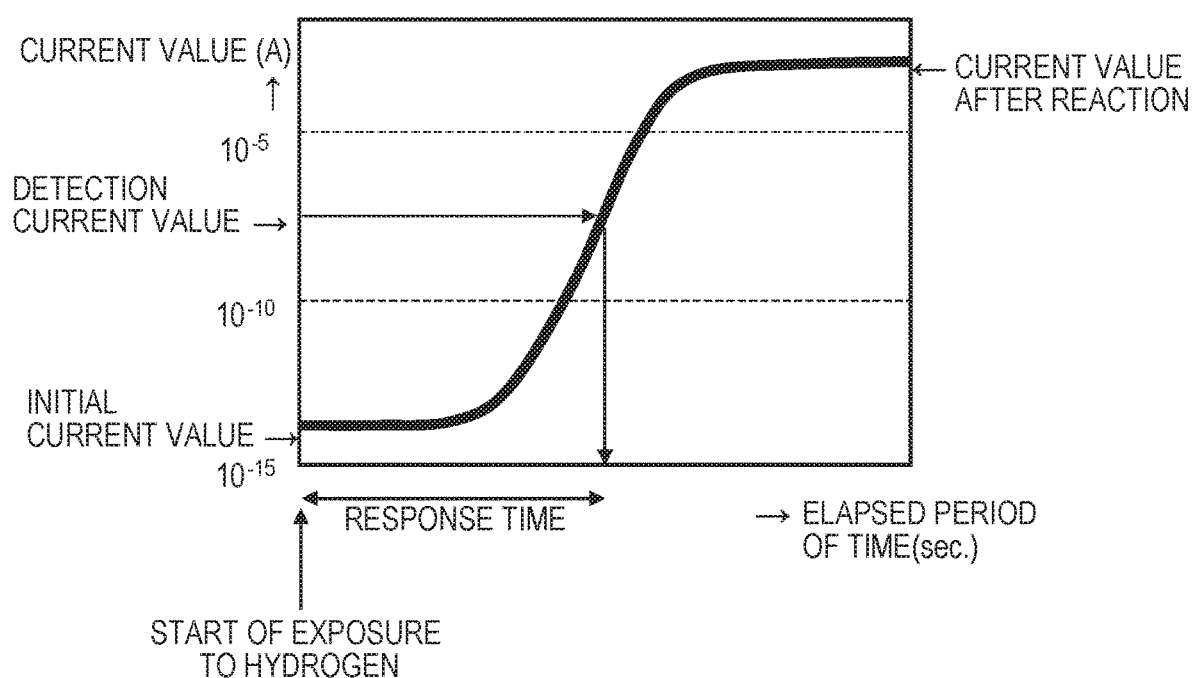
FIG. 1 is a graph for schematically showing a change in current value of a reducing gas detection material according to an embodiment of the present invention with respect to an exposure time to a reducing gas.

Now, embodiments and Examples of the present invention are described.

The present invention is not limited to the embodiments and Examples described below, and may be modified within the scope of the invention.

<Reducing Gas Detection Material>

A reducing gas detection material according to an embodiment of the present invention includes a palladium compound and a carbon compound, and has reactivity with a reducing gas.

Examples of a reaction between the palladium compound of the reducing gas detection material according to this embodiment and the reducing gas are represented by the following formula (a) and formula (b). The formula (a) represents an example in which palladium oxide is used as the palladium compound, and hydrogen is used as the reducing gas. The formula (b) represents an example in which palladium oxide is used as the palladium compound, and ethylene is used as the reducing gas. When palladium oxide reacts with hydrogen or ethylene, which is the reducing gas, a divalent palladium atom (Pd(II)) is reduced to generate a zero-valent palladium atom (Pd(0)).

Pd(II)O + H$_2$ ⟶ Pd(0) + H$_2$O  (a)

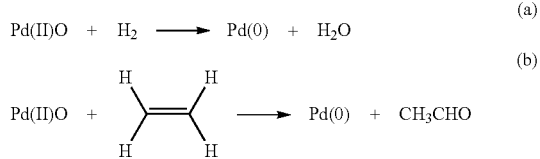

(b)

When the palladium compound reacts with the reducing gas, the palladium atom is reduced, and the valence is changed from 2 to 0. Through the reduction of the palladium atom, the reducing gas detection material is changed in color from ocher to black, and the conductivity of the palladium compound is changed, with the result that a large change occurs in electrical conductivity of the reducing gas detection material. The reducing gas that can be detected with the reducing gas detection material according to this embodiment is not limited to hydrogen or ethylene, and the reducing gas detection material can also detect, for example, formaldehyde, carbon monoxide, hydrogen sulfide, sulfur dioxide, and nitrous oxide.

In Japan Journal of Applied Physics, vol. 6, page 779 (1967), there is described that the electrical conductivity of a palladium oxide film is about 1 $\Omega^{-1}$ cm$^{-1}$ (room temperature). A reducing gas detection sensor is configured to detect a change in conductivity caused by change from the divalent palladium atom to the zero-valent palladium atom. The present inventors have conducted extensive investigations, and as a result, have found that, when a carbon compound is mixed with the palladium compound, the electrical conductivity of the reducing gas detection material before being exposed to the reducing gas can be decreased without decreasing the reactivity between the palladium compound and the reducing gas and the sensitivity of the reducing gas detection material.

Further, the present inventors have found that, when the palladium compound contains metallic palladium (zero-valent palladium atom (Pd(0))) together with palladium oxide (divalent palladium atom (Pd(II))), the reducing gas detection material exhibits a short response time. When the number of atoms of the palladium oxide and the number of atoms of the metallic palladium are represented by PO and PM, respectively, and a ratio $R_P$ of the number of atoms of the metallic palladium with respect to the total of the PO and the PM is represented by the following expression, the $R_P$ is preferably 0.17 or more and 0.45 or less.

$R_P$=PM/(PM+PO)

Examples of the palladium compound that can be used in the reducing gas detection material according to this embodiment include an inorganic salt, an oxide, a sulfide, and a halogen compound each containing a divalent palladium atom (Pd(II)). Specific examples thereof include palladium oxide, palladium sulfide, palladium chloride, palladium bromide, palladium sulfate, and palladium hydroxide.

In addition, the carbon compound that can be used in the reducing gas detection material according to this embodiment is a compound derived from a carboxylic acid or an alcohol. When the carboxylic acid or alcohol is mixed with the palladium compound, followed by heating, the carboxylic acid or alcohol is converted into the carbon compound derived from the carboxylic acid or alcohol. That is, the carbon compound in this embodiment is a compound obtained by converting a carboxylic acid, an alcohol, or a mixture thereof through a reaction with the palladium compound. The carbon compound in the reducing gas detection material is one kind of compound having a C—C single bond, a C—H bond, a C=C double bond, and an OH group or a mixture of a plurality of kinds of the compounds based on XPS analysis and IR spectrum analysis. The carbon compound may contain an unreacted alcohol. The carbon compound may be aliphatic hydrocarbon or aliphatic hydrocarbon hydroxide.

Examples of the carboxylic acid may include: monocarboxylic acids, such as acetic acid, propionic acid, butyric acid, isobutyric acid, valeric acid, isovaleric acid, pivalic acid, caproic acid, enanthic acid, caprylic acid, cyclohexylacetic acid, benzoic acid, and phenylacetic acid; and dicarboxylic acids, such as oxalic acid, malonic acid, succinic acid, glutaric acid, adipic acid, fumaric acid, maleic acid, and phthalic acid.

Examples of the alcohol may include: monohydric alcohols, such as methanol, ethanol, propanol, isopropyl alcohol, butanol, s-butanol, t-butanol, pentanol, hexanol, cyclohexanol, phenol, benzyl alcohol, and phenethyl alcohol; and dihydric alcohols, such as ethylene glycol, propylene glycol, diethylene glycol, and catechol.

In addition, hydroxy acids each having a carboxyl group and a hydroxyl group, such as lactic acid, malic acid, citric acid, and hydroxybenzoic acid, may be used.

Further, as a raw material for the reducing gas detection material according to this embodiment, a carboxylic acid complex and/or an alcohol complex of a divalent palladium atom may be used. In addition, the reducing gas detection material may also be produced by forming a coating film of a palladium complex having a specific structure, and then changing the complex to a palladium compound and a carbon compound by heat treatment.

Specifically, the reducing gas detection material containing palladium oxide serving as the palladium compound and the carbon compound may be produced by applying a palladium acetate analog represented by the general formula (1) to form a coating film, and performing heat treatment. As the palladium acetate analog represented by the general formula (1), any one of a monomer, a dimer, a trimer, and a multimer may be used.

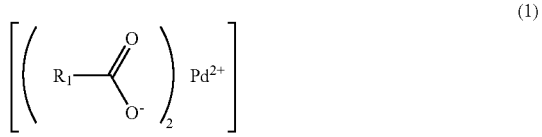

(1)

In the general formula (1), $R_1$ represents an alkyl group that may have a substituent, an aryl group that may have a substituent, or an aralkyl group that may have a substituent.

$R_1$ may represent, for example, a methyl group, an ethyl group, a propyl group, an isopropyl group, a butyl group, a s-butyl group, a t-butyl group, a pentyl group, a hexyl group, a cyclohexyl group, a pentyl group, an octyl group, a phenyl group, a tolyl group, a benzyl group, or a phenethyl group.

When a ratio R (=C/(P+C)) of the number C of carbon atoms contained in the carbon compound with respect to the total of the number P of palladium atoms contained in the palladium compound and the number C of carbon atoms is set to 0.50 or more and 0.95 or less in the reducing gas detection material according to this embodiment, the electrical conductivity of the reducing gas detection material before being exposed to the reducing gas is significantly decreased.

Specifically, when the ratio R of the number of carbon atoms falls within the above-mentioned range, the electrical conductivity of the reducing gas detection material is from $1\times10^{-8}\Omega^{-1}$ cm$^{-1}$ to $1\times10^{-11}\Omega^{-1}$ cm$^{-1}$ at room temperature. This electrical conductivity is smaller than the electrical conductivity (1 $\Omega^{-1}$ cm$^{-1}$) of the palladium oxide film described in Japan Journal of Applied Physics, vol. 6, page 779 (1967) by from 7 orders of magnitude to 10 orders of magnitude. The significantly small electrical conductivity is considered to be caused by the fact that the carbon compound inhibits the conductivity of the palladium compound. Meanwhile, when the reducing gas detection material according to this embodiment is exposed to the reducing gas, and a divalent palladium atom in the palladium compound is reduced to zero-valent palladium, the electrical conductivity of the reducing gas detection material is significantly increased. Thus, in the reducing gas detection material according to this embodiment, a difference in electrical conductivity before and after the exposure to the reducing gas is significantly large as compared to that of the related-art palladium oxide film. Therefore, when the reducing gas detection material according this embodiment is used in a reducing gas detection sensor, a sensor having high sensitivity can be provided.

FIG. 1 is a graph for schematically showing a change in current value at a time when any one of reducing gas detection sensor illustrated in FIG. 4A to FIG. 4C described later, which uses the reducing gas detection material according to this embodiment, is exposed to hydrogen. The horizontal axis represents an elapsed period of time from the start of exposure of a sensor element to hydrogen, and the vertical axis represents the value of a current flowing through the reducing gas detection material. An initial current value before exposure to hydrogen is a current value in a standby state, and when the current value reaches a detection current value, the reducing gas detection material and the reducing gas detection sensor according to this embodiment can detect a reducing gas. In addition, a period of time taken for the current value to reach the detection current value is a response time. The detection current value may be appropriately set by design operation of a detection circuit of the reducing gas detection sensor.

When the electrical conductivity of the reducing gas detection material before being exposed to the reducing gas is small, the current value in the standby state can be suppressed to be low in the reducing gas detection sensor configured to detect the electrical conductivity of the reducing gas detection material based on a change in current value. An application voltage for measuring a current value in the reducing gas detection sensor may be appropriately set. As a result, the power consumption during operation of the reducing gas detection sensor can be suppressed, and the application range of the reducing gas detection sensor is enlarged. For example, the reducing gas detection sensor can be driven by a general small battery. Further, the reducing gas detection sensor can be used for a long period of time without replacing a battery. In addition, through shortening of the response time, a reducing gas detection sensor capable of performing safety management at a higher level can be obtained. Therefore, the reducing gas detection sensor using the reducing gas detection material according to this embodiment can be used in a moving body, such as an electric vehicle, as well as in a storage house of a reducing gas.

(Method of Producing Reducing Gas Detection Material)

One example of a method of producing the reducing gas detection material according to an embodiment of the present invention includes subjecting a divalent palladium complex to heat treatment. In addition, another example of the method of producing the reducing gas detection material includes obtaining a mixture of the palladium compound and the carbon compound or further includes subjecting the obtained mixture to heat treatment. Specifically, a solution or a dispersion liquid of a divalent palladium complex is applied onto a substrate, and the coating film thus obtained is subjected to heat treatment to obtain a reducing gas detection material. Alternatively, a solution or a dispersion liquid of a palladium compound and a carbon compound is applied onto a substrate, and the coating film thus obtained is subjected to heat treatment as required to obtain a reducing gas detection material.

As a solvent that can be used in the solution or the dispersion liquid of the palladium compound and the carbon compound, there are given, for example, ethyl acetate, butyl acetate, toluene, chloroform, and dimethylformamide.

As a method of applying the solution or the dispersion liquid of the palladium compound and the carbon compound, there are given, for example, spin coating, dipping, casting, and bar coating. Of those, spin coating is preferred because the thickness of the reducing gas detection material can be regulated by adjusting the number of rotations of spin coating.

It is preferred that the heat treatment be performed at a temperature of 60° C. or more and 150° C. or less. In particular, when a coating film is heated at a temperature of 60° C. or more and 120° C. or less, a suitable carbon compound is generated through a reaction between palladium and a carbon compound, and thus, a reducing gas detection material having improved sensitivity can be obtained. In addition, when the coating film is heated at a temperature of 110° C. or more and 140° C. or less, the ratio $R_P$ of the number of atoms of the metallic palladium with respect to a total of the number of divalent palladium atoms and the number of zero-valent palladium atoms can be set to fall within a suitable range, and thus, a reducing gas detection material which achieves a short response time can be obtained. Through the reaction between the palladium and the carbon compound, the number C of carbon atoms in the reducing gas detection material becomes smaller than the number C of carbon atoms in the solution or the dispersion liquid of the palladium compound and the carbon compound. Thus, it is preferred that the palladium compound and the carbon compound be used so that the ratio R of the number C of carbon atoms with respect to the total of the number P of palladium atoms and the number C of carbon atoms in the reducing gas detection material is 0.50 or more and 0.95 or less. In order to measure the numbers of divalent palladium atoms and zero-valent palladium atoms and the number of carbon atoms in the reducing gas detection material, for example, an X-ray photoelectron spectrometer may be used, and the ratio $R_P$ and the ratio R may be determined based on the measured values of the numbers of atoms.

<Identification of Palladium Component in Reducing Gas Detection Material>

Figure 2:
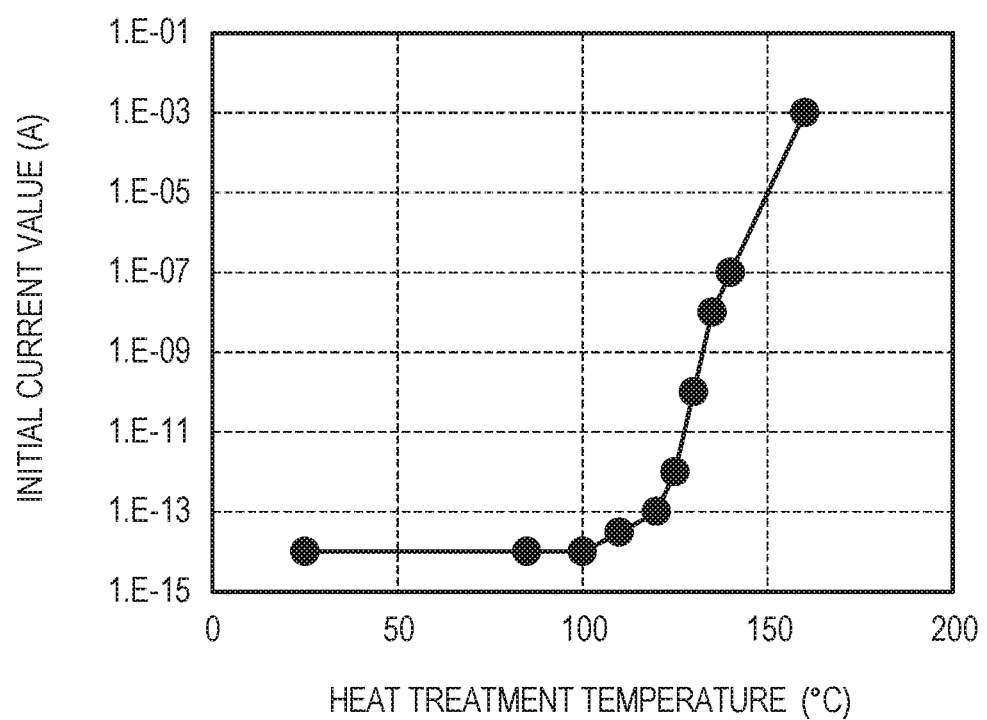
FIG. 2 is a graph for showing a relationship between a heat treatment temperature at a time of production of the reducing gas detection material according to the embodiment of the present invention and an initial current of the reducing gas detection material.

FIG. 2 is a graph for showing a relationship between the heat treatment temperature at a time of production of the reducing gas detection material according to this embodiment and an initial current of the reducing gas detection material. The heat treatment was performed by retention at each temperature for 2 hours, and after that, an initial current value was measured at 25° C. As a result, the initial current exhibits a value of $10^{-14}$ A at a treatment temperature of 100° C. or less. The initial current is abruptly increased at a treatment temperature of 110° C. or more and reaches a value of $10^{-3}$ A at a treatment temperature of 160° C. In FIG. 2, the reducing gas detection material using a palladium acetate analog as a raw material is shown.

The increase in initial current value in association with the increase in heat treatment temperature is considered to occur as follows. When the palladium acetate analog is subjected to heat treatment (100° C. or less), palladium oxide is generated. When the temperature is further increased, the palladium compound is reduced by heating to generate metallic palladium. As a result, the resistance value of the reducing gas detection material is decreased, and the current value is increased. The foregoing is supported by the following facts (1) and (2) at a time when the application voltage is set to 0.1 V: (1) the current value ($10^{-3}$ A) after the reaction in which the palladium compound is changed to metallic palladium through exposure to hydrogen as shown in FIG. 1 and the value of the initial current of the reducing gas detection material at a time when the heat treatment temperature is set to 160° C. as shown in FIG. 2 are substantially the same value ($10^{-3}$ A); and (2) the color of the reducing gas detection material after the hydrogen exposure reaction of the reducing gas detection material and the color of the reducing gas detection material after the heat treatment at 160° C. are both changed to black that is unique to metallic palladium. Thus, it is considered that the presence amount of metallic palladium is increased in the reducing gas detection material in association with the increase in temperature at a time of heat treatment, and the initial current value of the reducing gas detection material is increased in association therewith.

In order to clarify a change in oxidation state of the palladium atoms in the reducing gas detection material, the palladium compound in the reducing gas detection material was analyzed. Measurement was performed by grazing incidence X-ray diffractometry and X-ray photoelectron spectroscopy. Essential points of the result of each measurement are described below together.

In the grazing incidence X-ray diffractometry, a broad diffraction peak attributable to divalent palladium atoms (Pd(II)) was observed in the vicinity of 2θ=33° in the reducing gas detection material at a heat treatment temperature of from 60° C. to 140° C. Meanwhile, a peak attributable to zero-valent palladium atoms (Pd(0)) was observed in the vicinity of 2θ=40° and 2θ=47° in the reducing gas detection material at a treatment temperature of 160° C. From the above-mentioned measurement, the presence of palladium oxide in the reducing gas detection material at a heat treatment temperature of from 60° C. to 140° C. and the presence of metallic palladium in the reducing gas detection material at a treatment temperature of 160° C. were clarified. Such result suggests that the amount of metallic palladium is increased as the treatment temperature approaches 160° C.

In the X-ray photoelectron spectroscopy, focus was given on the binding energy (335 eV to 338 eV) of Pd (3d(5/2)) of palladium atoms. When focus was given on the spectrum of Pd (3d(5/2)) at a temperature of from 60° C. to 110° C., a sharp spectrum was observed at 337.5 eV attributable to the spectrum of divalent palladium atoms, and the result supporting the presence of the divalent palladium atoms was obtained. This result supports the above-mentioned result of X-ray diffraction. Further, as the treatment temperature was increased to as high as 130° C. and 160° C., the binding energy was shifted to low energy (336.4 eV (in the case of a temperature of 130° C.) and 335.9 eV (in the case of a temperature of 160° C.)). The shift of the binding energy of Pd (3d(5/2)) to a low energy side indicates an increase in amount of zero-valent palladium atoms, that is, metallic palladium.

As described above, based on the change in initial current value and the measurement results of the grazing incidence X-ray diffractometry and the X-ray photoelectron spectroscopy, it was found that the palladium compound in the coating film formed by applying palladium acetate was changed in valence by the heat treatment as shown in Table 1.

TABLE 1

| Heat treatment temperature | Palladium compound component |
|---|---|
| Around room temperature | Palladium acetate (Pd(II)) |
| 60° C. to 100° C. | Palladium oxide (Pd(II)) |
| 110° C. to 140° C. | Palladium oxide (Pd(II)) + metallic palladium (Pd(0)) |
| 160° C. or more | Metallic palladium (Pd(0)) |

<Improvement of Response Speed by Metallic Palladium>

Another important parameter of the reducing gas detection sensor is a response time. The response time refers to a period of time to be taken from the contact of the sensor with the reducing gas to the detection of a change in electrical conductivity. In Nanotechnology, 21, 165503 (5 pp), 2010, the definition of the response time is not necessarily clear, but values read from FIG. 1 and FIG. 2 of this literature are from about 150 seconds to about 200 seconds, which cannot be said to be a practically short response time.

In order to perform safety management of a gas, it is desired that response to a gas be made within a short period of time. There has hitherto been no technology for achieving both the above-mentioned low power consumption derived from sensitivity and the shortened response time at a practical level.

In view of the above-mentioned problem, an object of the present invention is to provide a reducing gas detection sensor further exhibiting a short response time.

The reducing gas detection material of the reducing gas detection sensor according to this embodiment before exposure may contain metallic palladium in addition to palladium oxide. In this case, as described above, palladium oxide reacts with the reducing gas to be changed to metallic palladium, which causes a change in electrical conductivity. As a result of further investigations conducted by the present inventors, it has been found that, when the reducing gas detection material before exposure to a gas contains metallic palladium in addition to palladium oxide, the response time of the reducing gas detection sensor with respect to the reducing gas is shortened. The reason why the response time is shortened due to the presence of metallic palladium in a certain ratio in the reducing gas detection material before exposure to the reducing gas is considered as follows.

A change in current caused by exposure to a gas in the reducing gas detection sensor according to this embodiment is derived from a change in current in association with an increase in electrical conductivity involved in change of palladium oxide to metallic palladium in the reducing gas detection material. Therefore, when the reducing gas detection material contains metallic palladium, which is a product of the above-mentioned reaction, in a certain ratio from the initial state before exposure, the response time is shortened.

Figure 3:
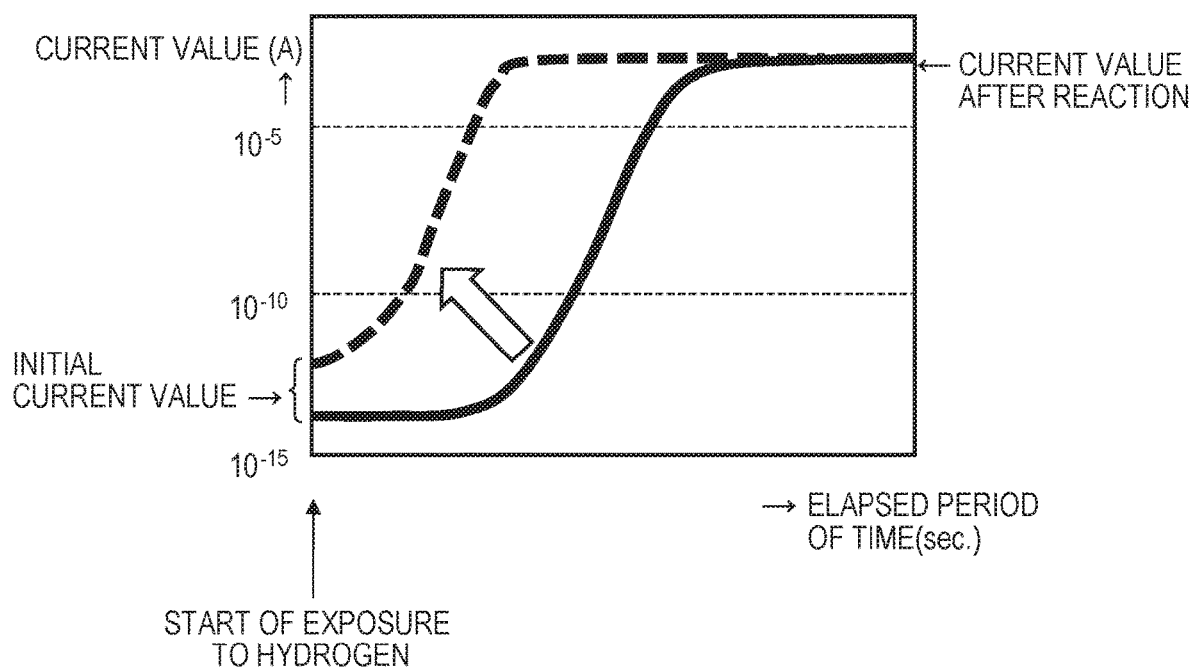
FIG. 3 is a graph for schematically showing a change over time in current value at a time of exposure to a reducing gas in each of the case of using a reducing gas detection material containing only palladium oxide (Pd(II)) and the case of using a reducing gas detection material containing palladium oxide (Pd(II)) and metallic palladium (Pd(0)).

The reason why the response time is shortened is described in more detail with reference to FIG. 3 that is a graph for schematically showing a change over time in current value at a time when the reducing gas detection material is exposed to the reducing gas. The solid line represents the case in which the reducing gas detection material contains only palladium oxide as the palladium compound, and the broken line represents the case in which the reducing gas detection material contains palladium oxide and metallic palladium as the palladium compound. In the former case in which the reducing gas detection material contains only palladium oxide, the initial current value is $10^{-14}$ A, and an increase in current starts after an elapse of a certain period of time. In the latter case in which the reducing gas detection material contains palladium oxide and metallic palladium, the reducing gas detection material contains metallic palladium before exposure to the reducing gas, and hence the initial current is large. Further, an increase in current starts immediately after the start of the exposure to the reducing gas, and hence the response time is shortened. In FIG. 3, for example, when focus is given on the period of time taken for the current to reach $10^{-5}$ A, the response time is improved (shortened) by about twice in the reducing gas detection material containing palladium oxide and metallic palladium as compared to the reducing gas detection material containing only palladium oxide.

As described above, it has been clarified that, in the sensor configured to detect a change in current derived from change of palladium oxide to metallic palladium in the reducing gas detection material at a time of exposure to a gas, the response time can be improved (shortened) by mixing metallic palladium in palladium oxide in the reducing gas detection material in an initial state before exposure to the gas.

The present inventors have conducted further investigations and have estimated a presence ratio of metallic palladium in the reducing gas detection material, which is effective for the present invention.

The number of atoms of palladium oxide and the number of atoms of metallic palladium contained in the reducing gas detection material are represented by PO and PM, respectively, and the ratio $R_P$ of the number of atoms of metallic palladium contained in the reducing gas detection material is defined as described below.

$$R_P = PM/(PM+PO)$$

The present inventors have conducted investigations in order to estimate the above-mentioned ratio. As a result, the present inventors have found that, when metallic palladium is generated through a reduction reaction of palladium atoms, the film thickness of the reducing gas detection material is decreased. A change amount of the film thickness of the reducing gas detection material is considered to be proportional to the amount of the generated metallic palladium. Therefore, the ratio of metallic palladium in the reducing gas detection material can be estimated through use of the above-mentioned relationship.

Film thickness of palladium oxide=T(PO)
Film thickness of metallic palladium=T(PM)
Film thickness of mixed layer of metallic palladium and palladium oxide=T(PO+PM)

Then, the presence ratio $R_P$ of metallic palladium is represented by the following expression.

$$R_P = (T(PO)-T(PO+PM))/(T(PO)-T(PM))$$

For example, palladium in a reducing gas detection material produced by heat treatment at a temperature of 80° C. is present as palladium oxide. The film thickness of the reducing gas detection material in this case is 37 nm.

Palladium in a reducing gas detection material produced by heat treatment at a temperature of 120° C. is present as palladium oxide and metallic palladium. The film thickness of the reducing gas detection material in this case is 34 nm.

Palladium in a reducing gas detection material obtained by exposing the reducing gas detection material produced by heat treatment at a temperature of 80° C. to a hydrogen gas to cause a reaction for a sufficiently long period of time (24 hours) is present as metallic palladium. The film thickness of the reducing gas detection material in this case is 25 nm.

In view of the foregoing, the presence ratio $R_P$ of metallic palladium at a temperature of 120° C. is represented by the following expression.

$$R_P = (37-34)/(37-25) = 0.25$$

When the heat treatment is performed at a temperature of more than 150° C., the initial current value is increased as the presence ratio of metallic palladium in the reducing gas detection material is increased, and the initial current value approaches a current value after the reaction with the reducing gas, with the result that desired sensitivity is not obtained. Therefore, in order to achieve the reducing gas detection sensor having a short response time with high sensitivity, the upper limit of the ratio of metallic palladium in the initial state before exposure to the reducing gas is 0.45.

Similarly, the lower limit of the metallic palladium ratio can also be determined, and the lower limit is 0.17.

Specifically, the preferred ratio $R_P$ of the number of atoms of metallic palladium is 0.17 or more and 0.45 or less.

The treatment temperature of the heat treatment is preferably more than 100° C. and 150° C. or less, more preferably 110° C. or more and 140° C. or less.

There is no problem whatever shape the reducing gas detection material according this embodiment has, but it is preferred that the reducing gas detection material according to this embodiment have a film shape because the contact area with the reducing gas is increased. When the reducing gas detection material according to this embodiment has a film shape, the film thickness is preferably 5 nm or more and 1,000 nm or less, more preferably 10 nm or more and 500 nm or less.

(Method of Detecting Reducing Gas through Use of Reducing Gas Detection Material)

The reducing gas detection material according to this embodiment is configured to detect a reducing gas based on change of the reducing gas detection material at a time when palladium atoms are reduced through a reaction between the palladium compound and the reducing gas, and the valance is changed from 2 to 0. Specifically, when the palladium compound reacts with the reducing gas, the reducing gas detection material is changed in color from ocher to black, and a large change occurs in electrical conductivity of the reducing gas detection material. Thus, the method of detecting a reducing gas through use of the reducing gas detection material according to this embodiment can utilize a change in color and/or change in conductivity in the reducing gas detection sensor. In particular, when the reducing gas detection material according to this embodiment detects a reducing gas, the conductivity thereof is largely changed as described above. Therefore, as the method of detecting a reducing gas, a method that utilizes a change in conductivity is preferred. As a detection unit configured to measure a change in the property of the detection material caused by a reaction of the detection material with the reducing gas, for example, a contact-type conductivity measurement method involving measuring a conductivity of the reducing gas detection material based on a change in electrical conductivity between a pair of electrodes brought into electrical contact with the reducing gas detection material or a non-contact-type conductivity measurement method involving measuring a conductivity of the reducing gas detection material through use of a microwave may be used. The detection unit can also be configured to measure a change of an absorption wavelength of the detection material.

<Reducing Gas Detection Sensor>

A reducing gas detection sensor according to an embodiment of the present invention includes the above-mentioned reducing gas detection material and a unit configured to measure conductivity of the reducing gas detection material. As the unit configured to measure conductivity of the reducing gas detection material, for example, a contact-type conductivity measurement unit configured to measure conductivity of the reducing gas detection material based on a change in electrical conductivity between a pair of electrodes that are electrically brought into contact with the reducing gas detection material or a non-contact-type conductivity measurement unit configured to measure conductivity of the reducing gas detection material through use of a microwave may be used.

Now, embodiments of the reducing gas detection sensor using the contact-type conductivity measurement unit are described.

First Embodiment

In a first embodiment, a reducing gas detection sensor 100 (hereinafter sometimes referred to as "sensor 100") using the above-mentioned reducing gas detection material is described with reference to FIG. 4A.

Figure 4A:
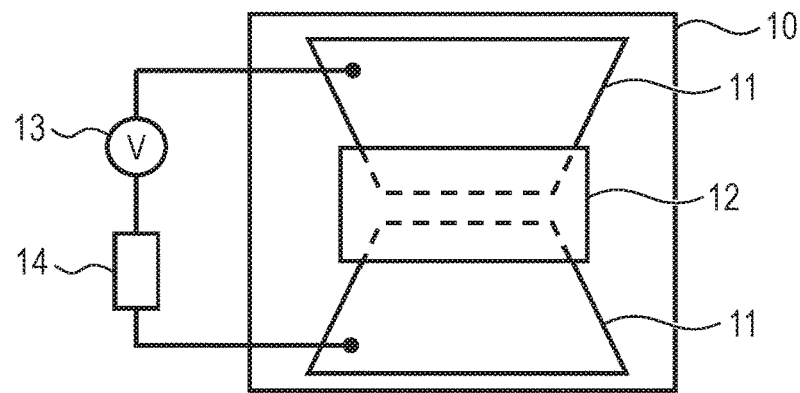
FIG. 4A, FIG. 4B, and FIG. 4C are each a schematic view for illustrating a configuration of a reducing gas detection sensor according to a first embodiment of the present invention.
Figure 4B:
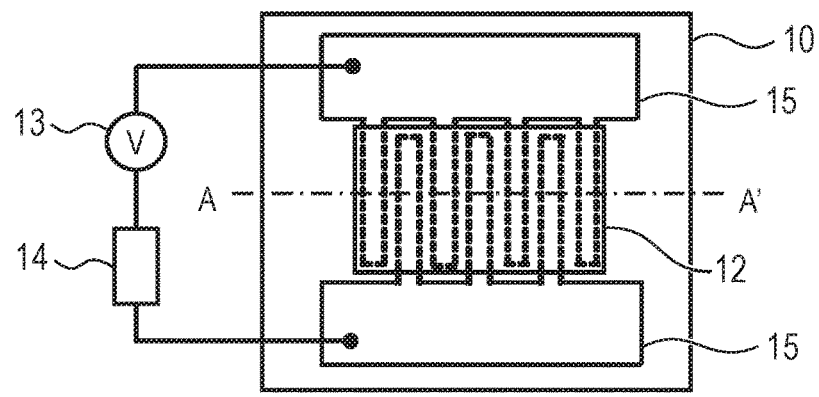
Figure 4C:
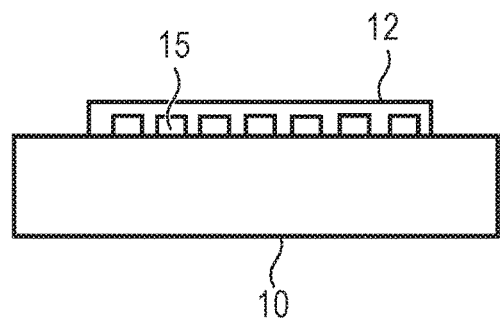

FIG. 4A is a schematic top view of the sensor 100 according to the first embodiment. The sensor 100 includes a substrate 10, a pair of electrodes 11, a reducing gas detection material 12, a power supply 13, and a measurement portion (detection circuit) 14.

As a material for the substrate 10, an insulator, for example, glass, quartz, or silicon may be used.

The pair of electrodes 11 is arranged on a surface of the substrate 10 so as to be opposed to each other. As a material for the pair of electrodes 11, a conductor, for example, a metal, a metal oxide, or an organic conductor may be used. Specific examples thereof include: metals, such as gold (Au) and aluminum (Al); metal oxides, such as ITO; and organic conductors, such as polyacetylene, poly p-phenylene, polythiophene, and PEDOT/PSS.

The shape of the pair of electrodes 11 may be appropriately designed in accordance with, for example, the kind of a reducing gas to be detected or the required sensitivity. In FIG. 4A, for example, there are illustrated the pair of opposed electrodes 11 each having a trapezoidal shape, with opposed portions each having a linear shape. However, the shape of the electrodes 11 is not limited thereto, and the electrodes 11 may have various shapes, such as a rectangle and a square. In addition, the shape of the opposed portions of the electrodes is not limited to a linear shape, and for example, may be a comb shape as in electrodes 15 of FIG. 4B. In the electrodes in which the opposed portions each have a comb shape as in the pair of electrodes 15, the effective length of an electrode (electrode length) along which the electrodes 15 are opposed to each other can be set to be longer than that of the electrodes 11 in which the opposed portions each have a linear shape. Therefore, even in the case of a substance having low electrical conductivity, a current value can be measured, and thus the sensitivity of the reducing gas detection sensor 100 can be enhanced.

Interelectrode distances between the electrodes 11 and the electrodes 15 are each preferably 0.05 µm or more and 100 µm or less, more preferably 0.05 µm or more and 30 µm or less, still more preferably 0.1 µm or more and 10 µm or less. In this case, each of the interelectrode distances is defined as a shortest distance of distances between the electrodes in a region in which the pair of electrodes are opposed to each other.

The reducing gas detection material 12 is arranged on the surface of the substrate 10. The reducing gas detection material 12 is arranged on the pair of electrodes 11 (15) so as to be brought into contact with the pair of electrodes 11 (15). In addition, the reducing gas detection material 12 is required to be arranged so as to be brought into contact with the reducing gas to be detected. Therefore, the reducing gas detection material 12 may be formed by forming a coating film of a solution or a dispersion liquid of a mixture of a palladium compound and a carbon compound on the surface of the substrate 10 having the electrodes 11 (15) on an electrode 11 (15) side by the above-mentioned application method and subjecting the coating film to heat treatment. FIG. 4C is a sectional view taken along the line A-A' of FIG. 4B. The reducing gas detection material 12 is arranged on the substrate 10 so as to cover the pair of opposed electrodes 15. Therefore, the reducing gas detection material 12 can be brought into contact with the reducing gas on a surface on an opposite side of the substrate 10.

The power supply 13 and the detection circuit 14 are electrically connected to each of the pair of electrodes 11 (15). The power supply 13 is configured to supply a voltage to the pair of electrodes 11 (15). The detection circuit 14 is configured to detect a change in conductivity of the reducing gas detection material 12 by measuring a change in electrical conductivity between the pair of electrodes 11. In addition, the detection circuit 14 is only required to measure a change in conductivity of the reducing gas detection material 12, and hence the detection circuit 14 may be configured to measure a change in at least one of resistance between the pair of electrodes 11 or electrical conductivity between the pair of electrodes 11.

As described above, the electrical conductivity of the reducing gas detection material before exposure to the reducing gas is suppressed. Therefore, the reducing gas detection sensor 100 according to the first embodiment can be a reducing gas detection sensor having low power consumption with high sensitivity. In addition, the reducing gas detection material before exposure to the reducing gas contains palladium oxide and metallic palladium, and hence the response time can be shortened.

In addition, in the related-art hydrogen gas detection sensor, a heater may be required in some cases at a time of use. However, in the reducing gas detection sensor 100 according to the first embodiment, the reducing gas can be detected at normal temperature. Therefore, the reducing gas detection sensor 100 does not require a heater and hence has a simple configuration, with the result that a reducing gas detection sensor that achieves both downsizing and reduction in cost can be obtained.

Second Embodiment

Figure 5:
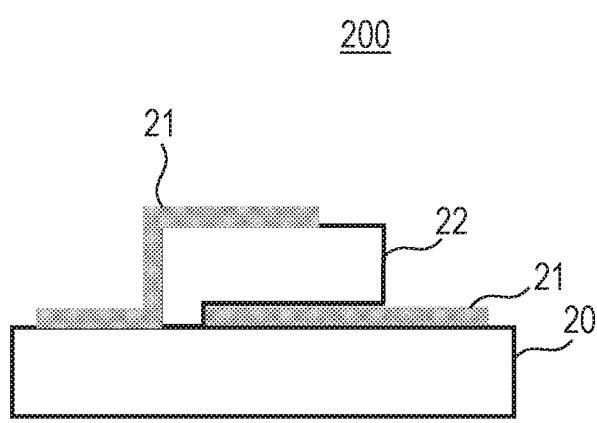
FIG. 5 is a schematic view for illustrating a configuration of a reducing gas detection sensor according to a second embodiment of the present invention.

In a second embodiment, the configuration of a reducing gas detection sensor 200 is described with reference to FIG. 5. FIG. 5 is a schematic sectional view for illustrating the configuration of the reducing gas detection sensor 200 according to the second embodiment. The reducing gas detection sensor 200 has the same configuration as that of the first embodiment except that the arrangement of a substrate 20, a pair of electrodes 21, and a reducing gas detection material 22 is different from that of the first embodiment.

In the second embodiment, the reducing gas detection material 22 is arranged on a surface of the substrate 20 so as to be sandwiched between the pair of electrodes 21 in a direction perpendicular to the surface of the substrate 20.

With the above-mentioned configuration, the sensitivity of the reducing gas detection sensor 200 can be improved as compared to that of the related-art reducing gas detection sensor. In addition, the power consumption can be decreased as compared to that of the reducing gas detection sensor 100 according to the first embodiment, and hence the reducing gas detection sensor 200 can be driven with a simple power supply, for example, a battery. Therefore, the reducing gas detection sensor 200 can be utilized for various applications.

<Utilization of Reducing Gas Detection Sensors According to Embodiments>

Figure 6:
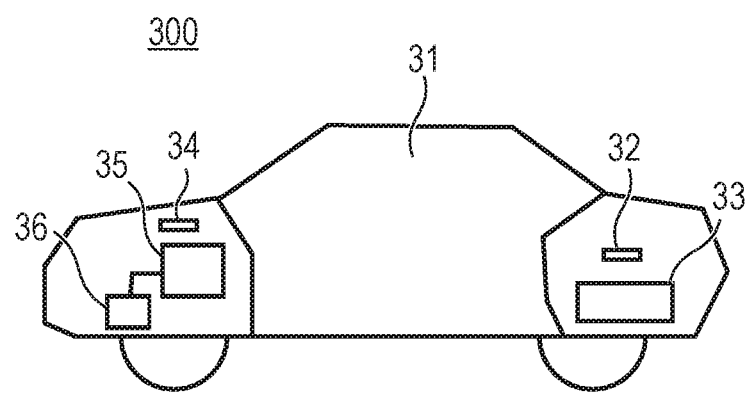
FIG. 6 is a schematic view for illustrating a configuration of a fuel-cell vehicle having the reducing gas detection sensor mounted thereon.

The reducing gas detection sensors according to those embodiments can be utilized in a storage facility of a reducing gas and a supply facility of a reducing gas. In addition, a fuel cell unit comprising a fuel cell can comprise the reducing gas detection sensor. Further, the reducing gas detection sensor can further comprise a determination unit to determine a leakage of the reducing gases and a notification unit to notify a result of a determination of the leakage of the reducing gases to users. Furthermore, as described in the first embodiment and the second embodiment, the reducing gas detection sensors according to those embodiments can be driven with low power consumption, and hence can also be utilized by being mounted on a moving body having a fuel cell that utilizes a reducing gas. As such moving body, there are given, for example, a vehicle, a motorcycle, and a drone, which have a fuel cell. Now, a vehicle 300 having a fuel cell that utilizes a hydrogen gas (hereinafter referred to as "fuel-cell vehicle") is described with reference to FIG. 6.

As the configuration of the fuel-cell vehicle 300, the configuration of a fuel-cell vehicle, which has been generally known, may be adopted, and the fuel-cell vehicle 300 includes a vehicle interior 31, reducing gas detection sensors 32 and 34, a hydrogen fuel tank 33, a fuel cell 35, and a motor 36. The fuel-cell vehicle 300 may have a configuration including only any one of the reducing gas detection sensors 32 and 34.

The hydrogen fuel tank 33 and the fuel cell 35 are arranged in spaces partitioned from the vehicle interior 31, respectively. The fuel cell 35 is configured to generate power through use of oxygen and a hydrogen gas supplied from the hydrogen fuel tank 33. The power generated by the fuel cell 35 is transmitted to the motor 36 and used as a drive force for driving the fuel-cell vehicle 300.

In order to detect a hydrogen gas, the reducing gas detection sensors 32 and 34 are provided in the same spaces as those of the hydrogen fuel tank 33 and the fuel cell 35 so as to be close thereto, respectively. As the reducing gas detection sensors 32 and 34, the reducing gas detection sensors described in the first embodiment and the second embodiment may be used, respectively.

The reducing gas detection sensors 32 and 34 can detect hydrogen with power consumption lower than that of the related-art reducing gas detection sensor. Therefore, even under a state in which the fuel cell 35 does not generate power in the fuel-cell vehicle 300, a hydrogen gas can be always detected. With this, a hydrogen gas, which has hitherto been able to be detected only at a time of power generation of the fuel cell 35, can be detected even at a time when the fuel cell 35 does not generate power. Therefore, the safety management of the fuel-cell vehicle can be performed more reliably.

In addition, the sensors 100 and 200 described in the first embodiment and the second embodiment may be provided also in a hydrogen station, which is configured to store a hydrogen gas and supply the hydrogen gas to a moving body having a fuel cell, instead of the moving body.

Further, the sensors according to those embodiments utilize an irreversible oxidation-reduction reaction as described above. Therefore, even when the formation of metallic palladium from palladium oxide based on the reaction proceeds due to the prolonged period of use, and it becomes impossible to obtain desired reducing gas detection performance, the sensors can be continuously used while keeping desired performance by replacing the above-mentioned reactive layer.

EXAMPLES

The present invention is hereinafter described by way of Examples, but the present invention is not limited to the following Examples.

Example 1

A 1 wt % ethyl acetate solution of palladium acetate (produced by Sigma-Aldrich) was prepared, and the ethyl acetate solution was applied by spin coating onto each electrode having a comb shape patterned on a glass substrate to form a coating film. The spin coating was performed at 1,000 rotations/min for 30 seconds, and the film thickness of the coating film after the spin coating was 50 nm. The interelectrode distance between the electrodes was set to 5 μm, and the length of each of the electrodes was set to 80 cm. After the formation of the coating film, the coating film was subjected to heat treatment at 60° C. for 2 hours to produce a reducing gas detection material, and a reducing gas detection sensor having the configuration of the reducing gas detection sensor 100 illustrated in FIG. 4B was manufactured.

(1) Identification of Component in Reducing Gas Detection Material

In order to identify a component in the reducing gas detection material produced as described above, X-ray photoelectron spectroscopy (XPS) was performed. As a measurement device, Quntera SXM manufactured by ULVAC-PHI, Incorporated was used, and as measurement conditions, Al monoKα serving as an X-ray source, a sample angle of 45°, and a beam of 100 μmΦ, 1.25 W, and 15 kV were used. In an XPS spectrum of the reducing gas detection material produced as described above, a peak corresponding to a carboxyl group in palladium acetate disappeared as compared to a sample that was not subjected to heat treatment. Meanwhile, there was a peak of a spectrum (285.0 eV) corresponding to a carbon 1s electron derived from a C—C single bond, a C—H bond, or a C=C double bond. Due to the presence of this spectrum, it was confirmed that there was a carbon compound having a C—C single bond, a C—H bond, or a C=C double bond in the reducing gas detection material.

When focus was given to a spectrum corresponding to a palladium 3d electron, due to the presence of a spectrum (binding energy: 337.4 eV) corresponding to palladium oxide, it was confirmed that there was palladium oxide.

In addition, a ratio R of the number of carbon atoms with respect to a total of the number of palladium atoms and the number of carbon atoms, which was calculated based on each spectrum area intensity of the palladium 3d electron and the carbon 1s electron, was 78%.

(2) Measurement of Current Value

While a voltage of 0.1 V was applied to the pair of electrodes of the reducing gas detection sensor manufactured as described above, a mixed gas of 1 vol % of a hydrogen gas and 99 vol % of argon (hereinafter sometimes referred to as "1% hydrogen mixed gas") was introduced to the vicinity of the reducing gas detection sensor, and a current value was measured. An abrupt change in current value started 200 seconds after the introduction of the 1% hydrogen mixed gas, and the current value became constant 20 seconds after the start of the change in current value. A current value before the introduction of the mixed gas was $2 \times 10^{-13}$ A, and a current value after the introduction of the mixed gas was $3 \times 10^{-3}$ A. The sensitivity S was calculated by the expression (I) through use of those current values, and the sensitivity S was found to be $1 \times 10^{10}$. It was confirmed that the reducing gas detection material in the reducing gas detection sensor was changed in color from ocher to black before and after the exposure to the 1% hydrogen mixed gas. As described above, when the detection material of the Example 1 was exposed to the 1% hydrogen mixed gas, it was recognized that the electrical conductivity of the detection material of the Example 1 became lager than that of the detection material before the exposure.

Example 2

A reducing gas detection sensor was manufactured in the same manner as in Example 1 except that the temperature of the heat treatment in Example 1 was changed to 85° C. In the manufactured reducing gas detection sensor, X-ray photoelectron spectroscopy and measurement of current values were performed in the same manner as in Example 1, and the sensitivity S of the reducing gas detection sensor was calculated based on the obtained current values. The results are shown in Table 2. It was confirmed that the reducing gas detection material in the reducing gas detection sensor was changed in color from ocher to black before and after the exposure to the 1% hydrogen mixed gas.

Example 3

A reducing gas detection sensor was manufactured in the same manner as in Example 1 except that the heat treatment in Example 1 was performed at 100° C. for 2 hours. X-ray photoelectron spectroscopy and measurement of current values were performed in the same manner as in Example 1, and the sensitivity S of the reducing gas detection sensor was calculated based on the obtained current values. The results are shown in Table 2. It was confirmed that the reducing gas detection material in the reducing gas detection sensor was changed in color from ocher to black before and after the exposure to the 1% hydrogen mixed gas.

Example 4

A reducing gas detection sensor was manufactured in the same manner as in Example 1 except that the heat treatment in Example 1 was performed at 120° C. for 2 hours. X-ray photoelectron spectroscopy and measurement of current values were performed in the same manner as in Example 1, and the sensitivity S of the reducing gas detection sensor was calculated based on the obtained current values. The results are shown in Table 2. It was confirmed that the reducing gas detection material in the reducing gas detection sensor was changed in color from ocher to black before and after the exposure to the 1% hydrogen mixed gas.

Example 5

In the reducing gas detection sensor manufactured in Example 1, current values were measured in the same manner as in Example 1 except that the 1% hydrogen mixed gas was replaced by a mixed gas of 1 vol % of an ethylene gas and 99 vol % of argon (hereinafter referred to as "1% ethylene mixed gas") in the measurement of the current values. The results are shown in Table 2. It was confirmed that the reducing gas detection material in the reducing gas detection sensor was changed in color from ocher to black before and after the exposure to the 1% ethylene mixed gas.

Example 6

In the reducing gas detection sensor manufactured in Example 2, current values were measured in the same manner except that the 1% hydrogen mixed gas was replaced by the 1% ethylene mixed gas in the measurement of the current values. The results are shown in Table 2. It was confirmed that the reducing gas detection material in the reducing gas detection sensor was changed in color from ocher to black before and after the exposure to the 1% ethylene mixed gas.

Comparative Example 1

A reducing gas detection sensor was manufactured in the same manner as in Example 1 except that the temperature of the heat treatment in Example 1 was changed to a temperature lower than 60° C. However, when current values of the obtained reducing gas detection sensor were measured in the same manner as in Example 1, stable data was not able to be obtained. This is presumably because the generation of the palladium compound and the carbon compound was not sufficient in the heat treatment at a temperature lower than 60° C.

From the results of the grazing incidence X-ray diffractometry and the X-ray photoelectron spectroscopy, it was confirmed that palladium oxide and metallic palladium were mixed together in the reducing gas detection material subjected to the heat treatment at 110° C.

(2) Measurement of Current Value

While a voltage of 0.1 V was applied to the pair of electrodes of the reducing gas detection sensor manufactured as described above, a change in current value was measured while a mixed gas containing a reducing gas to be detected was introduced to the vicinity of the sensor. A change in current value after the introduction of the mixed gas was observed, and a period of time (response time) taken for the current value to reach $10^{-6}$ A or $10^{-8}$ A was investigated. As the mixed gas, a 1% hydrogen mixed gas was used.

(3) Measurement of Sensitivity S

The measurement was performed by measuring an electrical conductivity between the electrodes before the mea-

TABLE 2

| Example | Gas to be detected | Presence ratio of carbon atom R | Current value before gas exposure (A) | Current value after gas exposure (A) | Sensitivity S | Heat treatment temperature/time |
|---|---|---|---|---|---|---|
| 1 | Hydrogen | 78% | $2 \times 10^{-13}$ | $3 \times 10^{-3}$ | $10^{10}$ | 60° C./2 hours |
| 2 | Hydrogen | 65% | $5 \times 10^{-13}$ | $3 \times 10^{-3}$ | $10^{10}$ | 85° C./2 hours |
| 3 | Hydrogen | 76% | $2 \times 10^{-13}$ | $1 \times 10^{-3}$ | $10^{10}$ | 100° C./2 hours |
| 4 | Hydrogen | 55% | $1 \times 10^{-13}$ | $5 \times 10^{-3}$ | $10^{10}$ | 120° C./2 hours |
| 5 | Ethylene | 79% | $7 \times 10^{-12}$ | $6 \times 10^{-3}$ | $10^{9}$ | 60° C./2 hours |
| 6 | Ethylene | 63% | $2 \times 10^{-13}$ | $3 \times 10^{-3}$ | $10^{10}$ | 85° C./2 hours |

Each of the reducing gas detection sensors having a reducing gas detection material containing palladium oxide and a carbon compound in Examples 1 to 6 had a sensitivity of about $1 \times 10^{10}$ and was found to have significantly high sensitivity as compared to the reducing gas detection sensor having a sensitivity S of 45 described in Nanotechnology, 21, 165503 (5 pp), 2010.

Example 7

A 1 wt % ethyl acetate solution of palladium acetate trimer (produced by Tokyo Chemical Industry Co., Ltd.) was prepared, and the ethyl acetate solution was applied by spin coating onto each electrode having a comb shape patterned on a glass substrate to form a coating film. The spin coating was performed at 1,000 rotations/min for 20 seconds, and the interelectrode distance between the electrodes was set to 5 μm. In addition, the length of each of the electrodes was set to 80 cm. After the formation of the coating film, the resultant was subjected to heat treatment by being kept in a constant-temperature oven at 110° C. for 2 hours to manufacture a reducing gas detection sensor having the configuration of the reducing gas detection sensor 100 illustrated in FIG. 4B.

(1) Identification of Component in Reducing Gas Detection Material

In order to identify a component in the reducing gas detection material produced as described above, grazing incidence X-ray diffractometry and X-ray photoelectron spectroscopy were performed.

For the grazing incidence X-ray diffractometry, X'Pert MRD manufactured by Malvern Panalytical Ltd. was used. In addition, for the X-ray photoelectron spectroscopy measurement, Quntera SXM manufactured by ULVAC-PHI was used.

surement of the current values and an electrical conductivity between the electrodes after the measurement of the current values. The sensitivity S was calculated by the expression (1) in the same manner as in Nanotechnology, 21, 165503 (5 pp), 2010 through use of the measured electrical conductivities before and after the current response experiment:

$$S=(G_H-G_N)/G_N \qquad (I)$$

where $G_H$ represents an electrical conductivity after a reaction with the reducing gas, and $G_N$ represents an electrical conductivity before a reaction with the reducing gas.

In Example 7, the measured current value was proportional to the electrical conductivity of the reactive layer, and hence the sensitivity S was calculated based on the measured current value.

In Example 7, the initial current value of the reducing gas detection sensor was $10^{-13}$ A. The response times taken for the current value to reach $10^{-6}$ A and $10^{-8}$ A from the start of exposure to the 1% hydrogen mixed gas were 100 seconds and 75 seconds, respectively. The sensitivity S was $1 \times 10^{10}$. The response time was improved by twice or more as compared to those in Comparative Examples 2 to 4 described later in which the heat treatment was performed at a temperature of from 25° C. to 100° C. It was found that the reducing gas detection sensor of Example 7 is a hydrogen gas detection sensor which achieves both high sensitivity and short response time.

The evaluation results of the reducing gas detection sensor of Example 7 are shown in Table 3.

Example 8

A reducing gas detection sensor was manufactured by performing the same operation as that of Example 7 except that the heat treatment was performed by storage in a constant-temperature oven at 120° C. for 2 hours. In the same manner as in Example 7, from the results of the grazing incidence X-ray diffractometry and the X-ray photoelectron spectroscopy, it was confirmed that palladium oxide and metallic palladium were mixed together in the reducing gas detection material.

In Example 8, the initial current value of the reducing gas detection sensor was $10^{-13}$ A. The response times taken for the current value to reach $10^{-6}$ A and $10^{-8}$ A from the start of exposure to the 1% hydrogen mixed gas were 60 seconds and 50 seconds, respectively. The sensitivity S was $1 \times 10^{10}$. The response time was improved by three times or more (shortened to ⅓ or less) as compared to those in Comparative Examples 2 to 4 described later in which the heat treatment was performed at a temperature of from 25° C. to 100° C. It was found that the reducing gas detection sensor of Example 8 is a hydrogen gas detection sensor which achieves both high sensitivity and short response time.

The results are shown in Table 3.

Example 9

A reducing gas detection sensor was manufactured by performing the same operation as that of Example 7 except that the heat treatment was performed by storage in a constant-temperature oven at 125° C. for 2 hours. In the same manner as in Example 7, from the results of the grazing incidence X-ray diffractometry and the X-ray photoelectron spectroscopy, it was confirmed that palladium oxide and metallic palladium were mixed together in the reducing gas detection material.

In Example 9, the initial current value of the reducing gas detection sensor was $10^{-12}$ A. The response times taken for the current value to reach $10^{-6}$ A and $10^{-8}$ A from the start of exposure to the 1% hydrogen mixed gas were 50 seconds and 40 seconds, respectively. The sensitivity S was $1 \times 10^{9}$. The response time was improved by four times or more (shortened to ¼ or less) as compared to those in Comparative Examples 2 to 4 described later in which the heat treatment was performed at a temperature of from 25° C. to 100° C. It was found that the reducing gas detection sensor of Example 9 is a hydrogen gas detection sensor which achieves both high sensitivity and short response time.

The results are shown in Table 3.

Example 10

A reducing gas detection sensor was manufactured by performing the same operation as that of Example 7 except that the heat treatment was performed by storage in a constant-temperature oven at 130° C. for 2 hours. In the same manner as in Example 7, from the results of the grazing incidence X-ray diffractometry and the X-ray photoelectron spectroscopy, it was confirmed that palladium oxide and metallic palladium were mixed together in the reducing gas detection material.

In Example 10, the initial current value of the reducing gas detection sensor was $10^{-10}$ A. The response times taken for the current value to reach $10^{-6}$ A and $10^{-8}$ A from the start of exposure to the 1% hydrogen mixed gas were 40 seconds and 30 seconds, respectively. The sensitivity S was $1 \times 10^{7}$. The response time was improved by five times or more (shortened to ⅕ or less) as compared to those in Comparative Examples 2 to 4 described later in which the heat treatment was performed at a temperature of from 25° C. to 100° C. It was found that the reducing gas detection sensor of Example 10 is a hydrogen gas detection sensor which achieves both high sensitivity and short response time.

The results are shown in Table 3.

Example 11

A reducing gas detection sensor was manufactured by performing the same operation as that of Example 7 except that the heat treatment was performed by storage in a constant-temperature oven at 135° C. for 2 hours. In the same manner as in Example 7, from the results of the grazing incidence X-ray diffractometry and the X-ray photoelectron spectroscopy, it was confirmed that palladium oxide and metallic palladium were mixed together in the reducing gas detection material.

In Example 11, the initial current value of the reducing gas detection sensor was $10^{-8}$ A. The response time taken for the current value to reach $10^{-6}$ A from the start of exposure to the 1% hydrogen mixed gas was 40 seconds. The sensitivity S was $1 \times 10^{4}$. The response time was improved by five times or more (shortened to ⅕ or less) as compared to those in Comparative Examples 2 to 4 described later in which the heat treatment was performed at a temperature of from 25° C. to 100° C. It was found that the reducing gas detection sensor of Example 11 is a hydrogen gas detection sensor which achieves both high sensitivity and short response time.

The results are shown in Table 3.

Example 12

A reducing gas detection sensor was manufactured by performing the same operation as that of Example 7 except that the heat treatment was performed by storage in a constant-temperature oven at 140° C. for 2 hours. In the same manner as in Example 7, from the results of the grazing incidence X-ray diffractometry and the X-ray photoelectron spectroscopy, it was confirmed that palladium oxide and metallic palladium were mixed together in the reducing gas detection material.

In Example 12, the initial current value of the reducing gas detection sensor was $10^{-7}$ A. The response time taken for the current value to reach $10^{-6}$ A from the start of exposure to the 1% hydrogen mixed gas was 35 seconds. The sensitivity S was $1 \times 10^{3}$. The response time was improved by five times or more (shortened to ⅕ or less) as compared to those in Comparative Examples 2 to 4 described later in which the heat treatment was performed at a temperature of from 25° C. to 100° C. It was found that the reducing gas detection sensor of Example 12 is a hydrogen gas detection sensor which achieves both high sensitivity and short response time.

The results are shown in Table 3.

Comparative Examples 2 to 5

Each of reducing gas detection sensors of Comparative Examples 2 to 5 was manufactured by performing the same operation as that of Example 7 except that the heat treatment was performed by storage in the constant-temperature oven at a temperature shown in Table 3 for 2 hours.

From the results of the grazing incidence X-ray diffractometry and the X-ray photoelectron spectroscopy performed in the same manner as in Example 7, the presence of metallic palladium in each of the reducing gas detection materials was not able to be confirmed in Comparative Examples 2 to 4. This is presumably because the heat treatment temperature was from 25° C. to 100° C. in the manufacturing of each of the reducing gas detection sensors of Comparative Examples 2 to 4, and metallic palladium was not generated at those treatment temperatures. In addition, the response time taken for the current value to reach $10^{-6}$ A from the start of exposure to the 1% hydrogen mixed gas was from 200 seconds to 300 seconds. Meanwhile, the sensitivity S exhibited a large value of $1 \times 10^{10}$.

Meanwhile, from the results of the grazing incidence X-ray diffractometry and the X-ray photoelectron spectroscopy performed in the same manner as in Example 7, the presence of palladium oxide in the reducing gas detection material was not able to be confirmed in Comparative Example 4. This is presumably because the heat treatment temperature was 160° C. in the manufacturing of the reducing gas detection sensor of Comparative Example 4, and the entire palladium oxide was changed to metallic palladium at this treatment temperature. Therefore, it was found that, even when the reducing gas detection sensor was exposed to the 1% hydrogen mixed gas, there was no change in current response time of the reducing gas detection sensor, and the reducing gas detection sensor did not respond to hydrogen.

The evaluation results of the reducing gas detection sensors of Comparative Examples 2 to 5 are shown in Table 3.

Example 13

A reducing gas detection sensor was manufactured by performing the same operation as that of Example 7 except that the palladium acetate trimer (produced by Tokyo Chemical Industry Co., Ltd.) was replaced by palladium acetate, and the heat treatment was performed by storage in the constant-temperature oven at 125° C. for 2 hours. In Example 13, the initial current value of the reducing gas detection sensor was $10^{-6}$ A. The response time taken for the current value to reach $10^{-6}$ A from the start of exposure to the 1% hydrogen mixed gas was 50 seconds. The sensitivity S was $1 \times 10^{9}$. It was found that the reducing gas detection sensor of Example 13 is a hydrogen gas detection sensor which achieves both high sensitivity and short response time.

Example 14

Current values and the sensitivity S were measured in the same manner as in Example 7 through use of the reducing gas detection sensor manufactured in Example 7 except that the 1% hydrogen mixed gas serving as a reducing gas was replaced by a 1% ethylene mixed gas. The initial current value of the reducing gas detection sensor was $10^{-6}$ A. The response time taken for the current value to reach $10^{-6}$ A from the start of exposure to the 1% ethylene mixed gas was 120 seconds. The sensitivity S was $1 \times 10^{10}$. It was found that the reducing gas detection sensor of Example 14 is an ethylene gas detection sensor which achieves both high sensitivity and short response time.

Example 15

The same operation as that of Example 10 was performed through use of the reducing gas detection sensor manufactured in Example 10 except that the 1% hydrogen mixed gas serving as a reducing gas was replaced by a 1% ethylene mixed gas. The initial current value of the reducing gas detection sensor was $10^{-10}$ A. The response time taken for the current value to reach $10^{-6}$ A from the start of exposure to the 1% ethylene mixed gas was 50 seconds. The sensitivity S was $1 \times 10^{6}$. It was found that the reducing gas detection sensor of Example 15 is an ethylene gas detection sensor which achieves both high sensitivity and short response time.

TABLE 3

| | Heat treatment temperature | Initial current (A) | Response time (sec) taken for current value to reach $10^{-6}$ A | Response time (sec) taken for current value to reach $10^{-8}$ A | Sensitivity S | Component |
|---|---|---|---|---|---|---|
| Comparative Example 2 | 25° C. | $10^{-14}$ | 200 to 300 | 200 to 300 | $10^{10}$ | Palladium acetate |
| Comparative Example 3 | 85° C. | $10^{-14}$ | 200 to 300 | 150 to 250 | $10^{10}$ | Palladium oxide |
| Comparative Example 4 | 100° C. | $10^{-14}$ | 200 to 300 | 150 to 250 | $10^{10}$ | Palladium oxide |
| Example 7 | 110° C. | $10^{-13}$ | 100 | 75 | $10^{10}$ | Palladium oxide + Metallic palladium |
| Example 8 | 120° C. | $10^{-13}$ | 60 | 50 | $10^{10}$ | Palladium oxide + Metallic palladium |
| Example 9 | 125° C. | $10^{-12}$ | 50 | 40 | $10^{9}$ | Palladium oxide + Metallic palladium |
| Example 10 | 130° C. | $10^{-10}$ | 40 | 30 | $10^{7}$ | Palladium oxide + Metallic palladium |
| Example 11 | 135° C. | $10^{-8}$ | 40 | — | $10^{4}$ | Palladium oxide + Metallic palladium |
| Example 12 | 140° C. | $10^{-7}$ | 35 | — | $10^{3}$ | Palladium oxide + Metallic palladium |
| Comparative Example 5 | 160° C. | $10^{-3}$ | No response | | | Metallic palladium |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-093370, filed May 14, 2018, and Japanese Patent Application No. 2018-093371, filed May 14, 2018, which are hereby incorporated by reference herein in their entirety.

What is claimed is:

1. A reducing gas detection material comprising:
a palladium oxide;
a metallic palladium; and
a carbon compound,
the reducing gas detection material having reactivity with a reducing gas,
wherein when a number of palladium atoms contained in the palladium oxide is represented by PO and a number of palladium atoms contained in the metallic palladium is represented by PM, a ratio $R_P$ of the number of palladium atoms contained in the metallic palladium with respect to a total of the number of palladium atoms contained in the palladium oxide and in the metallic palladium, as represented by expression $R_P=PM/(PM+PO)$, is 0.17 to 0.45.

2. The reducing gas detection material according to claim 1, wherein a ratio of a number of carbon atoms contained in the reducing gas detection material with respect to a total of a number of palladium atoms contained in the reducing gas detection material and the number of carbon atoms contained in the reducing gas detection material is 0.50 to 0.95.

3. The reducing gas detection material according to claim 1, wherein the reducing gas detection material has a film shape.

4. The reducing gas detection material according to claim 1, wherein the reducing gas comprises a hydrogen gas.

5. The reducing gas detection material according to claim 1, wherein the carbon compound is a compound or a mixture of compounds having a C—C single bond, a C—H bond, a C=C double bond, and/or an OH group.

6. The reducing gas detection material according to claim 1, wherein the carbon compound is an aliphatic hydrocarbon or an aliphatic hydrocarbon hydroxide.

7. The reducing gas detection material according to claim 1, wherein the carbon compound has non-volatility.

8. A reducing gas detection sensor comprising:
the reducing gas detection material according to claim 1; and
a detection unit configured to measure a change in a property of the detection material caused by a reaction of the detection material with the reducing gas.

9. The reducing gas detection sensor according to claim 8, wherein the detection unit measures a change in electrical conductivity of the detection material.

10. The reducing gas detection sensor according to claim 8, wherein the detection unit measures a change of an absorption wavelength of the detection material.

11. The reducing gas detection sensor according to claim 8, wherein an electrical conductivity of the detection material becomes larger when the detection material is exposed to a mixed gas of 1 vol % of a hydrogen gas and 99 vol % of argon.

12. The reducing gas detection sensor according to claim 8, further comprising
a pair of electrodes brought into electrical contact with the reducing gas detection material;
a power supply configured to supply a voltage to the pair of electrodes; and
a detection circuit configured to measure a change in electrical conductivity between the pair of electrodes.

13. The reducing gas detection sensor according to claim 12, wherein the pair of electrodes each have a comb shape.

14. The reducing gas detection sensor according to claim 8, further comprising
a determination unit to determine a leakage of the reducing gases, and
a notification unit to notify a result of a determination of the leakage of the reducing gases to users.

15. A fuel cell unit comprising:
the reducing gas detection sensor according to claim 8, and a fuel cell.

16. A moving body comprising the reducing gas detection sensor of claim 8 mounted thereon.

17. The moving body according to claim 16, wherein the reducing gas detection sensor is arranged in a vicinity of at least one of a hydrogen fuel tank or a fuel cell of the moving body.

18. The reducing gas detection material according to claim 1, wherein the reducing gas detection material contains only palladium as a metal species.

19. The reducing gas detection material according to claim 1, wherein electrical conductivity of the reducing gas detection material at room temperature before the reducing gas reacts with the reducing gas detection material is from $1\times10^{-8}\Omega^{-1}$ cm$^{-1}$ to $1\times10^{-11}\Omega^{-1}$ cm$^{-1}$.

* * * * *